(12) United States Patent
Lam et al.

(10) Patent No.: US 8,962,686 B2
(45) Date of Patent: Feb. 24, 2015

(54) METHOD AND MEDICATION FOR PREVENTION AND TREATMENT OF OCULAR HYPERTENSION AND GLAUCOMA

(75) Inventors: Dennis Shun Chiu Lam, Kowloon (CN); Johnson Yiu Nam Lau, Newport Beach, CA (US); Gary Hin Fai Yam, Pok Fu Lam (CN); Chi Pui Pang, Sha Tin (CN); Christopher Kai Shun Leung, Kowloon (CN); Haoyu Chen, Shantou (CN); Srinivas Kamalakara Rao, Chennai (IN); Dorothy Shu Ping Fan, Mid-Level (CN)

(73) Assignee: The Chinese University of Hong Kong, Shatin, N.T. (HK)

( * ) Notice: Subject to any disclaimer, the term of this patent is extended or adjusted under 35 U.S.C. 154(b) by 70 days.

(21) Appl. No.: 13/091,996

(22) Filed: Apr. 21, 2011

(65) Prior Publication Data

US 2012/0101074 A1 Apr. 26, 2012

Related U.S. Application Data

(60) Provisional application No. 61/328,987, filed on Apr. 28, 2010.

(51) Int. Cl.

| | | |
|---|---|---|
| *A01N 37/10* | (2006.01) | |
| *A61K 31/19* | (2006.01) | |
| *A61K 31/192* | (2006.01) | |
| *A61K 9/00* | (2006.01) | |
| *A61K 9/06* | (2006.01) | |
| *A61K 9/08* | (2006.01) | |
| *A61K 45/06* | (2006.01) | |
| *A61K 47/44* | (2006.01) | |

(52) U.S. Cl.
CPC .............. *A61K 31/192* (2013.01); *A61K 9/0048* (2013.01); *A61K 9/06* (2013.01); *A61K 9/08* (2013.01); *A61K 45/06* (2013.01); *A61K 47/44* (2013.01)
USPC ............ 514/570; 514/171; 514/563; 514/546

(58) Field of Classification Search
CPC . A61K 31/192; A61K 2300/00; A61K 45/06; A61K 47/44; A61K 9/0048; A61K 9/06; A61K 9/08
USPC .................................. 514/171, 563, 546, 570
See application file for complete search history.

(56) References Cited

U.S. PATENT DOCUMENTS

| | | | | |
|---|---|---|---|---|
| 2003/0138511 A1* | 7/2003 | Yamamoto et al. | ............ | 424/777 |
| 2004/0077612 A1* | 4/2004 | Mercep et al. | ................ | 514/175 |
| 2007/0027094 A1 | 2/2007 | Singh | | |
| 2008/0300292 A1 | 12/2008 | Letts et al. | | |

FOREIGN PATENT DOCUMENTS

| | | |
|---|---|---|
| WO | 02/13804 A2 | 2/2002 |
| WO | WO 2006052899 A2 * | 5/2006 |
| WO | 2007/047744 A2 | 4/2007 |

OTHER PUBLICATIONS

Pfeffer et al, Invest. Ophthalmol. Vis. Sci. Epub. Aug 2009; 5(1) 437-446.*
Calvo et al, The journal of pharmacy and pharmacology 48:Nov. 11, 1996 p. 1147-1152.*
Yam et al, IOVS, Apr. 2007, vol. 48, No. 4, 1683-1690.*
Sawant, Doctoral Thesis for North Eastern University, Nov. 2008.*
KH et al, Leukemia Aug. 1999;13(8):1258-65.*
International Search Report and Written Opinion corresponding to the PCT application No. PCT/US11/34158, date of mailing Jul. 8, 2011, 8 pages total.
Alward et al., 1998. "Clinical features associated with mutations in the chromosome 1 open-angle glaucoma gene (GLC1A)". *New England Journal of Medicine* 338:1022-1027. (1998).
Bennion et al., "Preventing misfolding of the prion protein by trimethylamine N-oxide". *Biochemistry*, vol. 43 (41), 12955-63. (2004).
Brusilow et al., "Urea cycle disorders: diagnosis, pathophysiology, and therapy". *Advances in Pediatrics*, vol. 43, 127-70. (1996).
Collins et al., "Oral sodium phenylbutyrate therapy in homozygous beta thalassemia: a clinical trial". *Blood*, vol. 85 (1), 43-49. (1995).
De Almeida et al., "Chemical Chaperones Reduce Endoplasmic Reticulum Stress and Prevent Mutant HFE Aggregate Formation", The Journal of Biological Chemistry vol. 282 (38), pp. 27905-27912. (2007).
Dover et al., "Induction of fetal hemoglobin production in subjects with sickle cell anemia by oral sodium phenylbutyrate". *Blood*, vol. 84 (1), 339-343. (1994).
Fingert et al., "Analysis of myocilin mutations in 1703 glaucoma patients from five different populations". *Human Molecular Genetics*, vol. 8(5):899-905. (1999).
Gong et al., "Trimethylamine N-oxide alleviates the severe aggregation and ER stress caused by G98R alphaA-crystallin". *Molecular Vision*, vol. 15, 2829-2840. (2009).
Jacobson at al., "Non-secretion of mutant proteins of the glaucoma gene *Myocilin* in cultured trabecular meshwork cells and in aqueous humor". *Human Molecular Genetics*, vol. 10 (2), 117-125. (2001).
Jia at al., "A natural osmolyte corrects the disease phenotype of mutant myocilin causing glaucoma". *Investigate Ophthalmology & Visual Science*, vol. 50 (8), 3743-3749. (2009).
Kolter at al., "Chemical chaperones-a new concept in drug research". *ChemBioChem*, vol. 4, 260-264. (2003).

(Continued)

*Primary Examiner* — Wu-Cheng Winston Shen
*Assistant Examiner* — Jean Cornet
(74) *Attorney, Agent, or Firm* — Kilpatrick Townsend & Stockton LLP

(57) ABSTRACT

An effective dose of a pharmaceutically acceptable phenylbutyrate salt such as sodium phenylbutyrate applied to human ocular tissues or through injection or other means prevents ocular hypertension and treats glaucoma in humans, leading to a new medical therapy for lowering the intraocular pressure via a mechanism different from the existing glaucoma medications. This compound can be formulated in combination with topical or other forms of steroids in prevention and treatment of steroid induced ocular hypertension and glaucoma.

10 Claims, 13 Drawing Sheets

(56) References Cited

OTHER PUBLICATIONS

Lee at al., "Induction of HSP70 promotes DF508 CFTR trafficking" *Am J Physiol Lung Cell Mol Physiol*,281: L58-L68.(2001).

Mulhern at al., "Cellular osmolytes reduce lens epithelial cell death and alleviate cataract formation in galactosemic rats". *Molecular Vision*, vol. 13, 1397-405. (2007).

Ozcan et al., "Chemical Chaperones Reduce ER Stress and Restore Glucose Homeostasis in a Mouse Model of Type 2 Diabetes" *Science*, vol. 313, 1137-1140 (2006).

Perlmutter, "Chemical chaperones: a pharmacological strategy for disorders of protein folding and trafficking". *Pediatric Research*, vol. 52 (6), 832-836. (2002).

Rubenstein et al., "Sodium 4-phenylbutyrate downregulates HSC70 expression by facilitating mRNA degradation" *Am J Physiol Lung Cell Mol Physiol*, vol. 281: L43-L51, (2001).

Singh at al., "Early aggressive intraocular pressure lowering, target intraocular pressure, and a novel concept for glaucoma care". *Survey Ophthalmology*, vol. 53 Supplement 1, S33-8. (2008).

Sit et al., "Effects of medications and surgery on intraocular pressure fluctuation". *Survey Ophthalmology*, vol. 53 Supplement 1, S45-55. (2008).

Tektas at al., "Morphologic changes in the outflow pathways of bovine eyes treated with corticosteroids". *Investigate Ophthalmology & Visual Science*, vol. 51 (8), 4060-6. (2010).

Wright et al., "Gene expression profile analysis of 4-phenylbutyrate treatment of IB3-1 bronchial epithelial cell line demonstrates a major influence on heat-shock proteins" *Physiol Genomics*, vol. 16, 204-211. (2004).

Yam et al., "Sodium 4-phenylbutyrate Acts as Chemical Chaperone on Misfolded Myocilin to Rescue Cells from Endoplasmic Reticulum Stress and Apoptosis". *Investigate Ophthalmology & Visual Science*, vol. 48 (4), 1683-1690. (2007).

Yam at al., "Aggregated myocilin induces russell bodies and causes apoptosis: implications for the pathogenesis of myocilin-caused primary open-angle glaucoma". *The American Journal of Pathology*, vol. 170 (1), 100-9. (2007).

Zou et al., "The molecular mechanism of stabilization of proteins by TMAO and its ability to counteract the effects of urea". *American Chemical Society*, vol. 124 (7), 1192-202.

Anon., CUHK Discovers Sodium 4-phenylbutyrate as a Potential New Glaucoma Drug (U.S. Provisional Patent Obtained), Press Release dated Aug. 17, 2010, (retrieved at http://www.cpr.cuhk.edu.hk/en/press_detail.php?id=846&s=).

Constad, et al., "Use of an Angiotensin Converting Enzyme Inhibitor in Ocular Hypertension and Primary Open-Angle Glaucoma," American Journal of Ophthalmology, vol. 105, No. 6, Jun. 15, 1988, 674-677.

Ferrer, "Highlights from the Annual Meeting of the Association for Research in Vision and Ophthalmology (ARVO) 2008: Eyes on Innovation," Drugs of the Future, vol. 33, No. 7, Jul. 2008, 633-643.

Jeng et al., "Retinal Ischemic Injury Rescued by Sodium 4-phenylbutyrate in a Rat Model," Experimental Eye Research, vol. 84, No. 3, Mar. 2007, 486-492.

Yam et al., "Sodium 4-phenylbutyrate Acts as a Chemical Chaperone on Misfold Myocilin to Rescue Cells from Endoplasmic Reticulum Stress in Aptosis," IOVS, vol. 48, o 4, Apr. 2007, 1983-1690.

Zode et al., "A Chemical Chaperone Rescues Glaucoma by Reducing ER Stress in a Novel Murine Model of Primary Open Angle Glaucoma," ARVO Annual Meeting, Abstract Search and Program Planner, vol. 2011, May 2011, 5917.

* cited by examiner

METHOD AND MEDICATION FOR PREVENTION AND TREATMENT OF OCULAR HYPERTENSION AND GLAUCOMA

BACKGROUND OF THE INVENTION

This invention relates to the prevention and treatment of ocular diseases and in particular ocular hypertension and glaucoma. Glaucoma is a leading cause of irreversible blindness worldwide. Loss of visual function is considered inevitable with progressive degeneration of the optic nerve.

The number of patients worldwide is expected to be increasing with aging population. It was estimated that there were 60.5 million glaucoma patients in 2010, increasing to 79.6 million by 2020 with 21.8 millions in China. A considerable proportion of patients with ocular hypertension and glaucoma fail to have optimal control of intraocular pressure. These patients often require surgical intervention which may end up with undesirable visual outcome. There is a need for a new class of medication for lowering as well as preventing intraocular pressure rise in susceptible individuals.

All current forms of glaucoma medical treatment are targeted at lowering the intraocular pressure. (Sit 2008; Singh, 2008) These include sympathetic nerve stimulants (nonselective stimulants such as epinephrine and alpha2 stimulants such as apraclonidine), sympathetic nerve blockers (beta blockers including timolol, befunolol, carteolol, nipradilol, betaxolol, levobunolol, and metipranolol and alpha1 blockers such as bunazosin hydrochloride), parasympathetic nerve agonists (pilocarpine), carbonic anhydrase inhibitors (acetazolamide and dorzolamide), and prostaglandin analogue (isopropyl unoprostone, latanoprost, travoprost, bimatoprost). These drugs either decrease the production of aqueous humor or increase the outflow facility through the trabecular meshwork and/or the uveoscleral outflow channels.

While aging, the use of topical steroids, myopia and a family medical history of glaucoma have been recognized as risk factors, lowering the intraocular pressure (IOP) remains the most effective approach in preventing visual loss in the glaucoma continuum. Although the pathologic mechanism for the development of glaucoma is not fully understood, it has been suggested that mutations in the myocilin gene (Jacobson, 2011; Jia 2009; Yam, 2007b), which may lead to an accumulation of defective myocilin gene product, might be a factor in a small subset that accounts for 2-4% of all the glaucoma patients (Alward, 1998; Fingert, 1999). If the above mechanism is correct, chaperones that reduce myocilin accumulation may be useful for this small group of patients. In reality, as most patients with glaucoma do not have a defective myocilin gene, this approach will be rendered inapplicable.

Sodium phenylbutyrate, (more specifically, a salt of 4-phenylbuytrate with structure shown in FIG. 1A), is a medication that has been used clinically to treat urea cycle disorders, sickle cell anemia and β-thalassemia (Brusilow, 1996; Collins, 1995; Dover, 1994.

Sodium phenylbutyrate is a short-chain fatty acid (FIG. 1B) and its chaperone effect has previously been shown to stabilize myocilin folding and facilitate intracellular trafficking and therefore reduce abnormal protein accumulation in cells that would lead to cell stress and death. (Yam, 2007a) It is therefore possible that patients with mutated myocilin gene defect can get beneficial effect from receiving sodium phenylbutyrate treatment. Oral administration of sodium phenylbutyrate has been shown very recently to rescue glaucoma phenotypes in mice expressing Y437H mutant myocilin transgene with normalization of elevated intraocular pressure when compared to untreated transgene mice (Zode et al., Association for Research in Vision and Ophthalmology 2011 Annual Meeting Abstract). Nonetheless, one would predict that this compound would have no effect on animals or patients with normal myocilin gene. As hereinafter shown, the opposite is true.

By way of support for the present invention but not as prior act, we found that sodium phenylbutyrate is effective in preventing and treating the intraocular pressure rise in an animal model of steroid-induced glaucoma in normal rabbits. (FIGS. 2A and 2B and FIG. 3). Such an animal model is commonly used for glaucoma research.

Moreover, if sodium phenylbutyrate is using its chaperone effect in preventing and treating the intraocular pressure rise in rabbits, one might predict that other chaperones may also work to lower the intraocular pressure. To explore this hypothesis, trimethylamine N-oxide (TMAO) was tested out using the same steroid-induced glaucoma model in rabbits. TMAO is another well known small-molecule chaperone (Gong, 2009; Kolter, 2003; Perlmutter, 2002); a natural osmolyte capable of stabilizing protein folding and acting as a protein stabilizer to protect ligand binding and polymerization against pressure inhibition. It improves folding and assembly of different proteins. Surprisingly, we found that TMAO was not effective at all in reducing the intraocular pressure rise as shown in the case of sodium phenylbutyrate. Specifically FIG. 4 illustrates the negative effect of trimethylamine N-oxide (TMAO) on dexamethasone-induced intraocular pressure changes. Fourteen New Zealand albino rabbits (7-week-old male) were divided into 5 groups. The right eyes received topical dexamethasone four times a day followed by topical TMAO (2, 10, 50, 100 and 300 mM) four times a day whereas the left eyes received topical dexamethasone four times a day followed by balanced salt solution, a physiological saline that acted as a control, four times a day. Topical TMAO did not prevent or treat the dexamethasone-induced intraocular pressure rise for the entire study period of 18 days (FIG. 4). The intraocular pressure in both eyes showed no significant difference. This suggests that prevention and treatment of elevation of steroid-induced intraocular pressure by sodium phenylbutyrate may not be related to chemical chaperone activity. This finding is very surprising.

The following references are pertinent to this disclosure:
1. Alward W L, Fingert J H, Coote M A, Johnson A T, Lerner S F, Junqua D, Durcan F J, McCartney P J, Mackey D A, Sheffield V C, and Stone E M. 1998. Clinical features associated with mutations in the chromosome 1 open-angle glaucoma gene (GLC1A). *New Engl J Med.* 338:1022-1027.
2. Bennion B J, DeMarco M L and Daggett V (2004) Preventing misfolding of the prion protein by trimethylamine N-oxide. *Biochemistry,* 43, 12955-63.
3. Brusilow, S. W. and Maestri, N. E. (1996) Urea cycle disorders: diagnosis, pathophysiology, and therapy. *Adv Pediatr,* 43, 127-70.
4. Collins, A. F., Pearson, H. A., Giardina, P., McDonagh, K. T., Brusilow, S. W. and Dover, G. J. (1995) Oral sodium phenylbutyrate therapy in homozygous beta thalassemia: a clinical trial. *Blood,* 85, 43-9.
5. Dover, G. J., Brusilow, S. and Charache, S. (1994) Induction of fetal hemoglobin production in subjects with sickle cell anemia by oral sodium phenylbutyrate. *Blood,* 84, 339-43.
6. Fingert J H, Heon E, Liebmann J M, Yamamoto T, Craig J E, Rait J, Kawase K, Hoh S T, Buys Y M, Dickinson J, Hockey R R, Williams-Lyn D, Trope G, Kitazawa Y, Ritch R, Mackey D A, Alward W L, Sheffield V C, and Stone E M. 1999. Analysis of myocilin mutations in 1703 glaucoma patients from five different populations. *Hum Mol Genet.* 8(5):899-905.
7. Gong, B., Zhang, L.Y., Pang, C. P., Lam, D. S. and Yam, G. H. (2009) Trimethylamine N-oxide alleviates the severe aggregation and ER stress caused by G98R alphaA-crystallin. *Mol Vis,* 15, 2829-40.
8. Jacobson N, Andrews M, Shepard A R, Nishimura D, Searby C, Fingert J H, Hageman G, Mullins R, Davidson B L, Kwon Y H, Alward W L, Stone E M, Clark A F, and Sheffield V C. 2001. Non-secretion of mutant proteins of the glaucoma gene myocilin in cultured trabecular meshwork cells and in aqueous humor. *Hum Mol Genet.* 10:117-25.
9. Jia, L. Y., Gong, B., Pang, C. P., Huang, Y., Lam, D. S., Wang, N. and Yam, G. H. (2009) A natural osmolyte corrects the disease phenotype of mutant myocilin causing glaucoma. *Invest Ophthalmol Vis Sci,* 50, 3743-3749.
10. Kolter T, and Wendeler M. 2003. Chemical chaperones—a new concept in drug research. *Chembiochem.* 4:260-264.
11. Mulhern, M. L., Madson, C. J., Kador, P. F., Randazzo, J. and Shinohara, T. (2007) Cellular osmolytes reduce lens epithelial cell death and alleviate cataract formation in galactosemic rats. *Mol Vis,* 13, 1397-405.
12. Perlmutter D H. 2002. Chemical chaperones: a pharmacological strategy for disorders of protein folding and trafficking *Pediatr Res.* 52:832-836.
13. Singh, K. and Shrivastava, A. (2008) Early aggressive intraocular pressure lowering, target intraocular pressure, and a novel concept for glaucoma care. *Surv Ophthalmol,* 53 Suppl1, S33-8.
14. Sit, A. J. and Asrani, S. (2008) Effects of medications and surgery on intraocular pressure fluctuation. *Surv Ophthalmol,* 53 Suppl1, S45-55.
15. Tektas, O. Y., Hammer, C. M., Danias, J., Candia, O., Gerometta, R., Podos, S. M. and Lutjen-Drecoll, E. (2010) Morphologic changes in the outflow pathways of bovine eyes treated with corticosteroids. *Invest Ophthalmol Vis Sci,* 51, 4060-6.
16. Yam G H F, Gaplovska-Kysela K, Zuber Ch and Roth J (2007) Sodium 4-phenylbutyrate Acts as Chemical Chaperone on Misfolded Myocilin to Rescue Cells from Endoplasmic Reticulum Stress and Apoptosis. *Invest Ophthalmol Vis Sci,* 48, 1683-1690.
17. Yam G H F, Gaplovska-Kysela K, Zuber Ch and Roth J (2007) Aggregated myocilin induces russell bodies and causes apoptosis: implications for the pathogenesis of myocilin-caused primary open-angle glaucoma. *Am J Pathol,* 170, 100-9.
18. Zou, Q., Bennion, B. J., Daggett, V. and Murphy, K. P. (2002) The molecular mechanism of stabilization of proteins by TMAO and its ability to counteract the effects of urea. *J Am Chem Soc,* 124, 1192-202.

SUMMARY OF THE INVENTION

According to the invention, a medication is provided for use in treating a disease that comprises an effective dose of a pharmaceutically acceptable salt of phenylbutyrate, and particularly sodium phenylbutyrate, in an appropriate solution or carrier, such as an ophthalmic solution, salve or cream. In use the solution or carrier is topically applied to ocular tissue or through periocular (including subconjunctival, subtenon, peribulbar, retrobulbar, and anterior juxtascleral depot), intraocular (intracameral and intravitreal), systemic intake (oral ingestion and parenteral injection), or via controlled or sustained release methods or other means, prevents ocular hypertension and treats glaucoma in humans, leading to a new medical therapy for lowering the intraocular pressure via a mechanism different from the existing glaucoma medications. This compound can be formulated or modified in combination with an anti-inflammatory steroid, a steroid prodrug or a cortisol-derived compound of different formulations and/or other currently available glaucoma medications in prevention and treatment of steroid induced ocular hypertension and glaucoma.

While we have shown that prevention and treatment of elevation of steroid-induced intraocular pressure by sodium phenylbutyrate is mostly likely not related to its chemical chaperone activity, we do not know the exact mechanism(s). It is possible that other activities of sodium phenylbutyrate including its effect on histone acetylation (acetylation), transcriptions and protein prenylation, and nitrogen scavenger activities are responsible for the intraocular pressure lowering effect herein reported.

There were four more surprising findings from experiments:

First, sodium phenylbutyrate was found to be useful for the prevention of steroid-induced intraocular pressure rise (FIG. 2).

Second, sodium phenylbutyrate was effective for lowering intraocular pressure in steroid-induced glaucoma (FIG. 3).

Third, the doses effective in and useful for reducing the increase of steroid-induced intraocular pressure were found to be extremely low, surprisingly much lower than the dose used for the treatment of urea cycle disorders, in which the chaperone effect is believed to be the therapeutic mechanism. In our animal experiments, the level of sodium phenylbutyrate was found to be effective with concentrations as low as 0.01 to 15 mM when applied 2-5 times a day (FIGS. 5 and 6).

Fourth, the pharmacodynamic effect was found to be extremely long-lasting, which is out of one's expectation. We found that topical sodium phenylbutyrate was able to suppress the intraocular pressure rise for a maximum of 18 days after the cessation of applications of the sodium phenylbutyrate eyedrops (FIG. 7).

The invention will be better understood by reference to the following detailed description in connection with the accompanying drawings.

BRIEF DESCRIPTIONS OF THE DRAWINGS

DETAILED DESCRIPTION OF SPECIFIC EMBODIMENTS

Figures 1A, 1B:
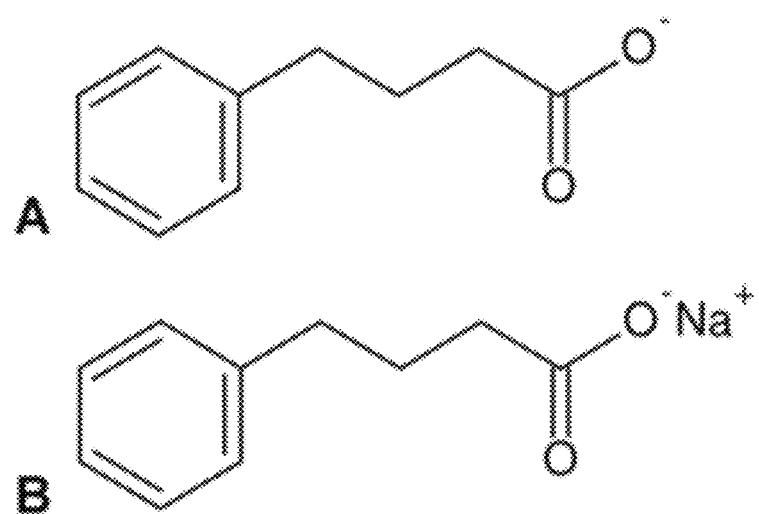
FIG. 1 is a diagram of the structure of 4-phenylbuytrate and the sodium salt of 4-Phenylbuytrate, a known compound, although its formulation as a targeted medication is novel.

A pharmaceutically acceptable salt of phenylbutyrate, especially sodium phenylbutyrate is suitable for use as a medication for treatment of ocular conditions. A formulation in an appropriate solution or inert carrier may be administered as either a parenteral or an oral preparation and can be prepared in the forms of, for example, ophthalmological preparation, injections (intravenous, or through one of the eye or periocular, intravitreal, subconjunctival, subtenon, peribulbar, retrobulbar, and intracameral), tablet, capsule, powder, granule, solution, and the like. These preparations can be prepared by known techniques by suitably adding known carriers. It is preferably used, among others, as an ophthalmological preparation, particularly preferably as an instillation, and such an ophthalmic preparation may be aqueous eye drop, non-aqueous eye drop, suspension eye drop, emulsion eye drop, eye ointment, and the like. The preparation can be produced by preparation methods known to those skilled in the art as a composition suitable for the dosage form by adding pharmacologically acceptable carriers such as tonicity agents, chelating agents, stabilizers, pH modifiers, preservatives, antioxidants, solubilizing agents, and thickening agents, if necessary.

An ophthalmic preparation is prepared by, for example, dissolving or suspending desired ingredients of the above-mentioned compounds in an aqueous solvent such as sterile purified water or physiological saline or a non-aqueous solvent such as vegetable oil including cottonseed oil, soybean oil, sesame oil, or peanut oil at a predetermined osmotic pressure and subjecting the solution or suspension to sterilization such as sterilization by filtration. When a salve or an eye ointment is prepared, an ointment base can be added in addition to the above-mentioned various ingredients. The above-mentioned ointment base is not particularly limited, but preferred examples thereof include oily bases such as petroleum jelly, liquid paraffin, and polyethylene, emulsion bases obtained by emulsifying the oil phase and the aqueous phase with a surfactant or the like, water-soluble bases comprising hydroxypropylmethylcellulose, carboxymethylcellulose, polyethylene glycol or the like.

It is known that the allosteric conversion from rabbit to human, based on plasma concentrations and calculation, is a factor of 1.9. If the applications including topical eyedrops, lotion, cream and others do not follow the allosteric conversion, the concentration identified to be effective in the animal models will be the same as in human patients. If they follow allosteric conversion, as well as systemic administration like oral, skin patch, or injections including subcutaneous, intramuscular and intravenous administrations, the calculated concentration may need to be adjusted by a factor of 1.9 higher for the plasma levels. Assuming that the plasma levels are the same as that of the target tissue level, the reverse conversion factor may be applied for the calculated doses applicable to humans.

Figure 2A:
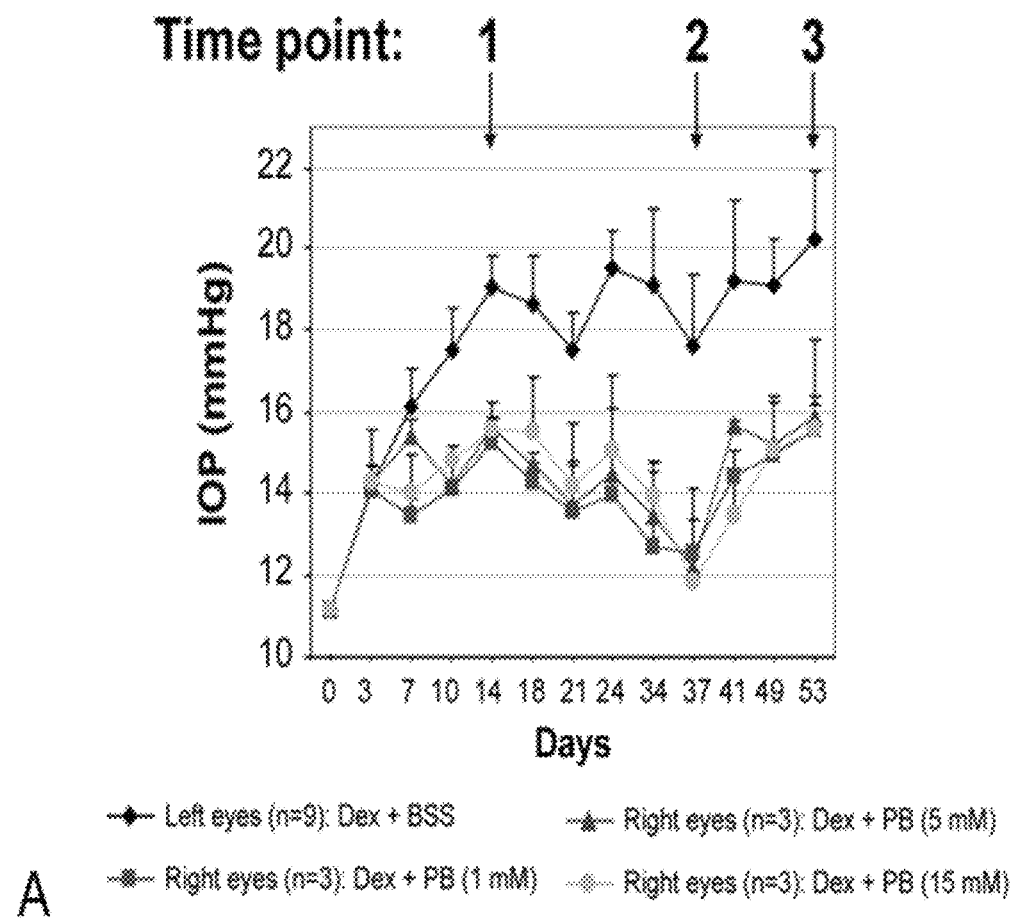
FIGS. 2A and 2B are a set of charts showing the effects of topical sodium phenylbutyrate (1, 5 and 15 mM) on preventing intraocular pressure elevation in a steroid-induced glaucoma model in rabbits.
Figure 2B:
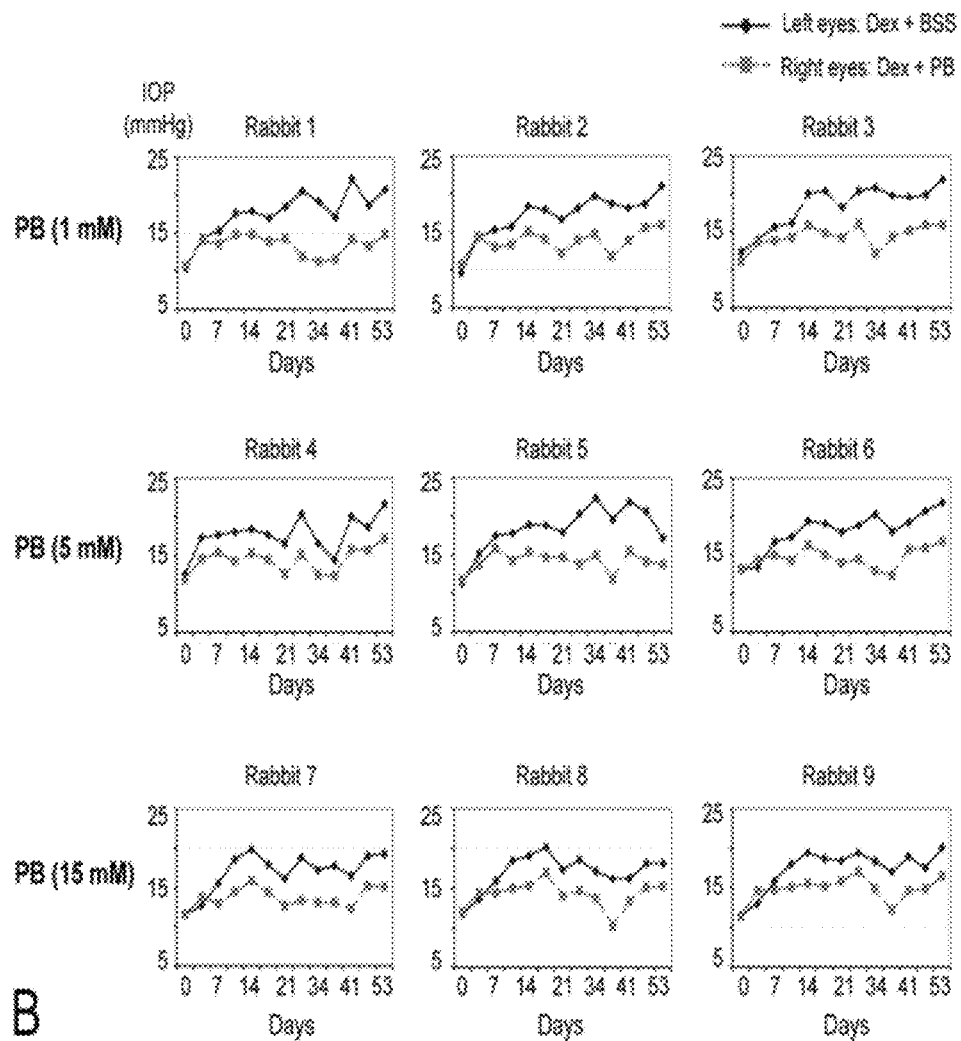

There are experimental data collected from our own experiments using an animal model of steroid induced glaucoma in rabbits showing the safety and effectiveness of a particular salt of sodium phenylbutyrate, the sodium phenylbutyrate, in preventing intraocular pressure rise and treating the elevated intraocular pressure. Dexamethasone, a commonly used steroid was used in all our experiments. Specifically FIGS. 2A and 2B are charts that illustrate the effect of sodium phenylbutyrate on preventing intraocular pressure (IOP) rise in a steroid-induced glaucoma model. Herein, nine 7-week-old male New Zealand albino rabbits were randomly divided into 3 groups and each of them received Dexamethasone (Dex) (MaxiDex containing 0.1% Dex, Alcon) 5 times a day in both eyes. In addition, topical sodium phenylbutyrate (PB) (Triple Crown America/TriButyrate, Inc. Perkasie, Pa.) in concentrations of 1, 5 or 15 mM were applied to their right eyes 5 times a day and a balanced salt solution (BSS), a physiological saline that acted as a control, to their left eyes 5 times a day. Intraocular pressure (IOP) was measured twice a week at an interval of 3-4 days by a masked technician. (A) IOP rise was observed after topical Dex had been applied to the left eyes (diamond line: Dex+BSS). Three time points (days 14, 37 and 53) were chosen for data analysis. Time point 1 (day 14) was a commonly adopted time point to obtain significant steroid-induced IOP rise; time point 2 (day 37) showed a maximum reduction of IOP rise; and time point 3 (day 53) was the time when the study ended. The mean baseline intraocular pressure (IOP) was 11.5 mmHg for both eyes. The percentage of reduction in IOP rise by PB was defined as ("Mean IOP rise in eyes with Dex+BSS" minus "Mean IOP rise in eyes with Dex+PB") divided by "Mean IOP rise in eyes with Dex+BSS"×100%.

By referring to FIG. 2A, the application of phenylbutyrate (PB) eye drops 5 times a day helped reduce Dex-induced IOP rise regardless of their concentrations. The amount of reduction of IOP rise was similar in all the 3 PB doses (square, triangle, circle lines, respectively) and the data were integrated and analyzed as one group. The percentages of mean reduction in IOP rise were 45.0%, 84.7% and 50.0% at the three time points on days 14, 37 and 53 respectively. FIG. 2B charts show the longitudinal profiles of IOP measurements of individual rabbits receiving Dex+BSS (left eye, diamonds line) and Dex+PB (right eye, squares line) respectively. Although chaperones are effective in enhancing protein trafficking and reducing intracellular accumulation of abnormal proteins, all of these animals had the normal myocilin gene and the IOP lowering effect of sodium phenylbutyrate should not be related to the enhanced trafficking of the mutated myocilin gene products. This surprising result has led to further investigation and characterization of the therapeutic effects of sodium phenylbutyrate.

Figure 3:
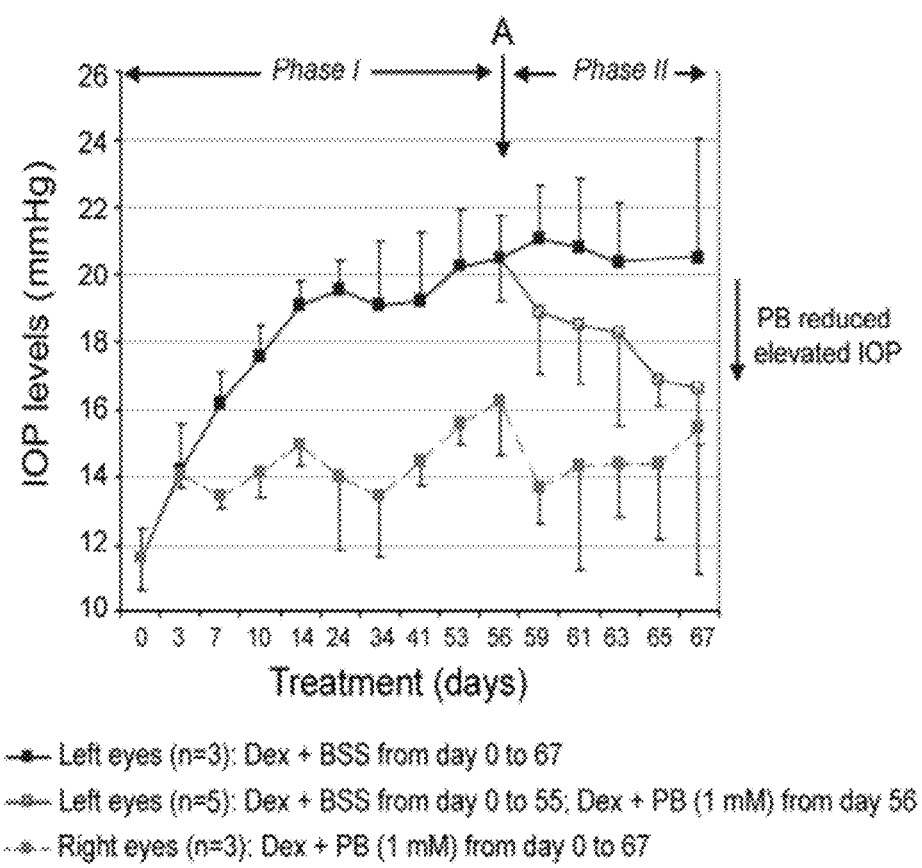
FIG. 3 is a diagram showing the effect of 1 mM topical sodium phenylbutyrate (PB) in reducing the elevated intraocular pressure (IOP) from steroid-induced IOP rise in rabbits.

On day 56 when Phase II of the experiment started, topical sodium phenylbutyrate (1 mM), instead of balanced salt solution, was applied to the left eyes of 5 rabbits (FIG. 3). The IOP was reduced from 20.5 mmHg on day 56 to 16.6 mmHg on day 67 (FIG. 3, brown line), representing a 19% reduction in IOP over a treatment period of 11 days. Moreover, the IOP level of 16.6 mmHg was very close to the mean IOP level of 15.4 mmHg on day 67 (FIG. 3, gray like) in the eyes that had been treated with PB in the concentration of 1 mM throughout both phases of the study. It is surprising to have the following observations: (1) as shown in FIGS. 2A and 2B, sodium phenylbutyrate is effective in preventing an increase in IOP associated with steroid eye-drop use (Phase I, treatment with sodium phenylbutyrate versus control, balance salt solution); and (2) as shown in FIG. 3, sodium phenylbutyrate is effective in lowering the IOP, as illustrated by the digression after check point A (FIG. 3, brown line).

Figure 4:
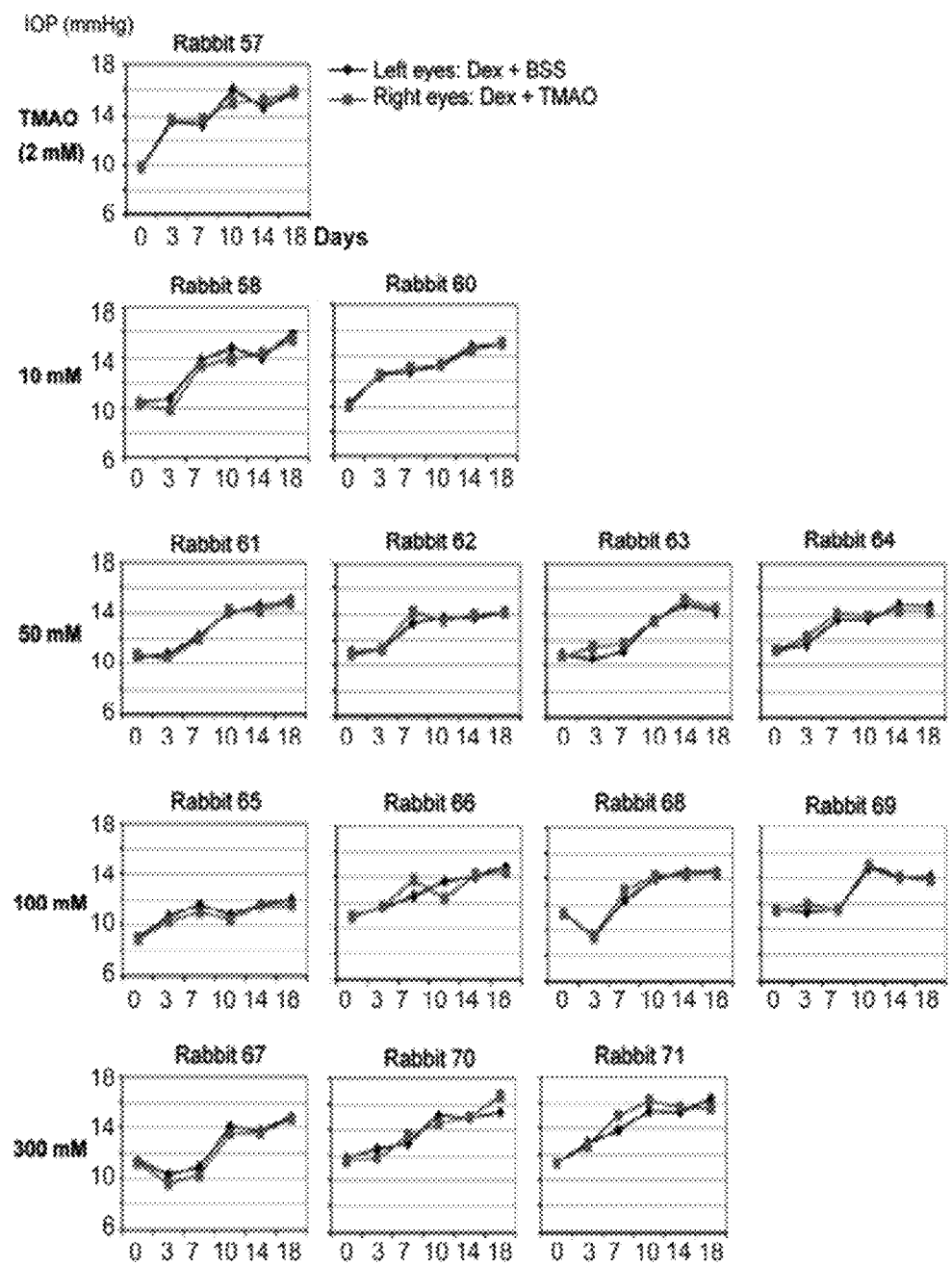
FIG. 4 is a set of charts showing Trimethylamine N-oxide (TMAO), a chemical chaperone that had no effect in the lowering of steroid-induced intraocular pressure (IOP) rise in rabbits.

FIG. 4 shows the negative results of Trimethylamine N-oxide (TMAO), a chemical chaperone, in lowering steroid-induced intraocular pressure (IOP) rise in rabbits. Fourteen 7-week-old male New Zealand albino rabbits received topical dexamethasone (Dex) (MaxiDex containing 0.1% Dex, Alcon) 4 times a day in both eyes. Topical trimethylamine N-oxide (TMAO) with concentrations varying from 2 mM to 300 mM was applied to the right eye whereas balance salt solution (BSS), a physiological saline that acted as a control, was applied to the left 4 times a day. All rabbits showed an increase in intraocular pressure (IOP) of up to 6 mmHg on day 14 compared with the baseline (day 0). TMAO did not prevent Dex-induced IOP rise for the entire study period of 18 days. The IOP in both eyes which were treated with Dex+BSS (left eyes, blue lines) and Dex+TMAO (right eyes, magenta lines) respectively showed no significant difference. This suggests that prevention of steroid-induced IOP rise by phenylbutyrate is probably not related to chemical chaperone activity.

Figure 5:
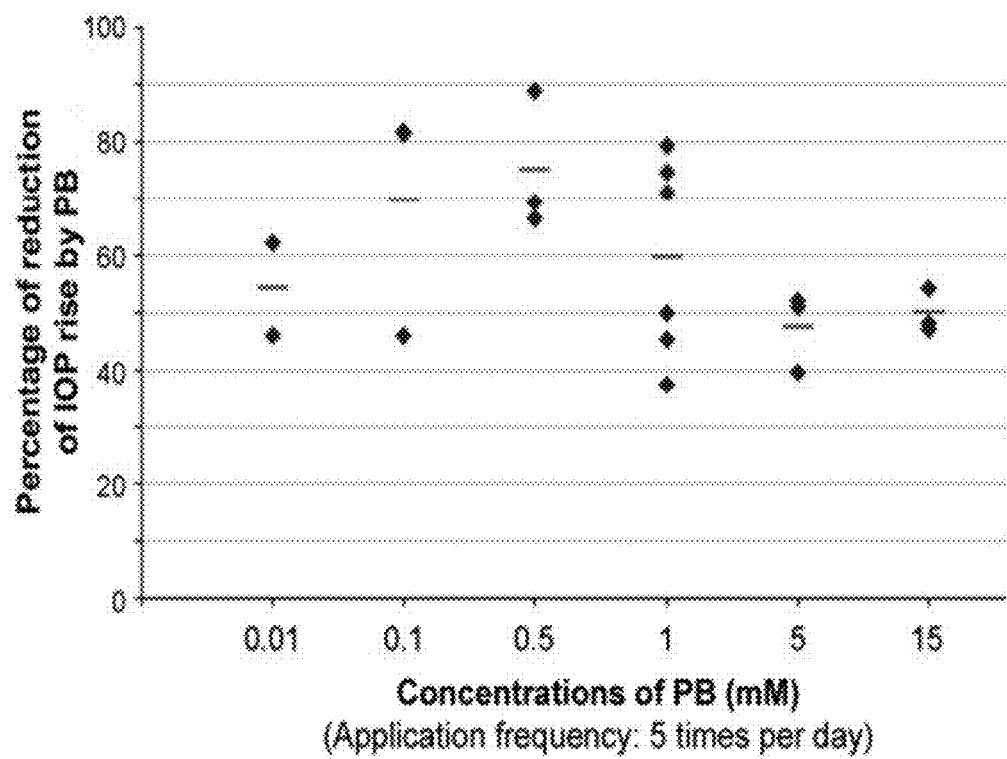
FIG. 5 is a chart showing the effective concentration of sodium phenylbutyrate in preventing steroid-induced IOP rise.

FIG. 5 illustrates the effective concentration of sodium phenylbutyrate in the prevention of steroid-induced intraocular pressure (IOP) rise. The right eyes of 18 rabbits, which were characterized as strong responders as they showed a >30% rise in steroid-induced intraocular pressure (IOP) from the baseline level on day 14, received topical dexamethasone (Dex, MaxiDex, Alcon) and sodium phenylbutyrate (PB) (0.01, 0.1, 0.5, 1, 5 and 15 mM) eye drops 5 times a day respectively. Their left eyes were treated with Dex+BSS. The IOP was measured twice a week. The percentage of reduction in IOP rise by PB was calculated based on the formula defined in [0035]. The diagram showed the percentages of reduction in IOP rise (diamonds) on day 14 with respect to the different dosages of PB (x-axis). The mean percentage of the reduction in IOP rise within the groups of different dosages of PB was represented by the (horizontal line). A dose-related reduction in steroid-induced IOP rise by PB was observed. For PB applied at doses varying from 0.1 to 1 mM, the reduction in steroid-induced IOP rise was between 59.7% and 74.9%. Other test doses showed a reduction of about 50%.

Figure 6:
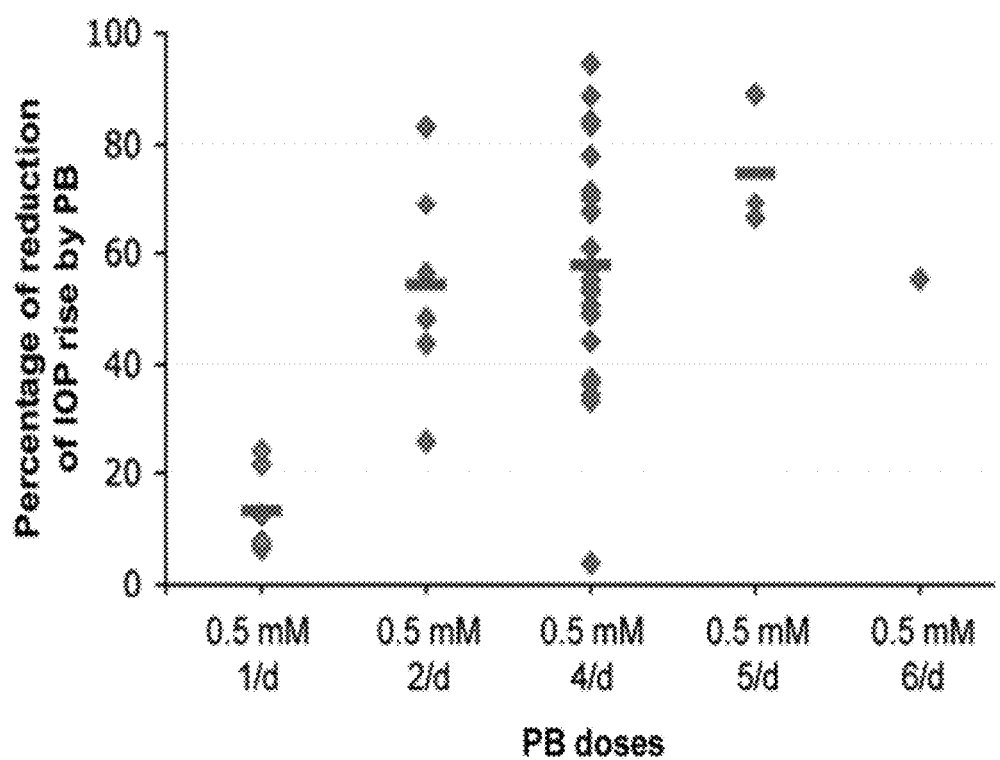
FIG. 6 is a chart showing the effect of application frequency of topical sodium phenylbutyrate on preventing steroid-induced IOP rise.

FIG. 6 illustrates the frequency-related effect of topical sodium phenylbutyrate (PB) on reducing steroid-induced intraocular pressure (IOP) rise. The right eyes of 43 rabbits received topical Dex+PB (0.5 mM) ranging from 1 to 6 times a day. The left eyes received Dex+BSS. IOP was measured twice a week. On day 14, the reduced IOP of individual eyes treated with Dex+PB was compared with the IOP of the contralateral eyes treated with Dex+BSS to obtain a percentage of IOP reduction (diamonds) and the mean percentage of IOP reduction within the group as represented by the (horizontal lines). The mean percentage of reduction in IOP was calculated based on the very same formula defined in [0036]. It was found that the mean percentage of reduction in IOP increase was highest (74.9%) in the eyes to which PB was applied 5 times a day. The corresponding percentages were 57.9%, 54.4% and 13.2% for eyes to which PB eye drops were applied 4, 2 and 1 time(s) a day respectively.

The effective concentration of sodium phenylbutyrate to be used topically in the compound ranges from 0.01 mM to 15 mM (FIGS. 2A and 2B and 5) and should be applied topically from 2 to 5 times a day (FIG. 6).

Figure 7:
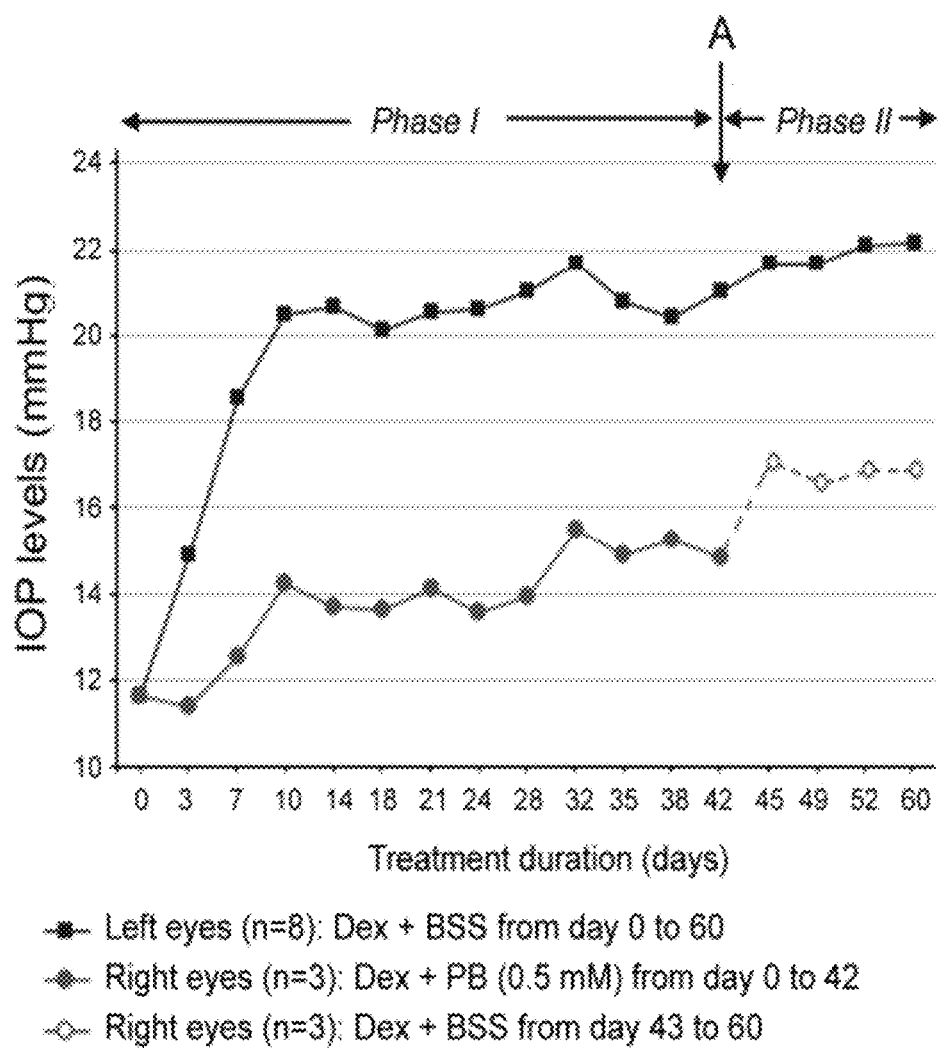
FIG. 7 is a diagram showing the long-lasting pharmacodynamic effect of sodium phenylbutyrate (PB) on preventing steroid-induced IOP rise after cessation of topical application in rabbits.

FIG. 7 shows the long-lasting pharmacodynamic effect by sodium phenylbutyrate (PB) on preventing steroid-induced IOP rise after cessation of topical application in rabbits. Eight rabbits were studied in this experiment. All their left eyes received Dex+BSS 5 times a day, from day 0 to day 60, the day when the experiment ended (squares line for both Phase I and Phase II). A significant IOP rise was observed in the first 10 days and the mean IOP from day 10 to day 60 was maintained at a level between 20 and 22 mmHg. The right eyes of 3 randomly-chosen rabbits were treated with Dex+PB (sodium phenylbutyrate, 0.5 mM) eye drops 5 times a day, from day 0 to day 42. IOP measurement showed a lessened Dex-induced IOP rise (solid brown line in Phase I), which was similar to previous observations. The IOP increased slowly in the first 10 days, and from day 10 to day 42, the mean IOP was maintained at a low level between 14 and 16 mmHg. On day 43, the treatment of the right eyes of the 3 rabbits changed from Dex+PB to topical Dex+BSS. Still, Dex+BSS eye drops were applied 5 times a day, until day 60 when the experiment ended (broken brown line in Phase II). With the cessation of topical PB, it was originally expected that the IOP would rise significantly and catch up with the IOP level in the left eyes, where no PB was applied (squares line), in about 10 days. Surprisingly, only a very mild increase in IOP by less than 2 mmHg was observed and the mean IOP level was maintained at about 16.5 mmHg. On day 60 when the experiment ended and the eyes had received treatment of Dex for 18 days), the IOP was stabilized at a level of 16.6 mmHg.

Figure 8:
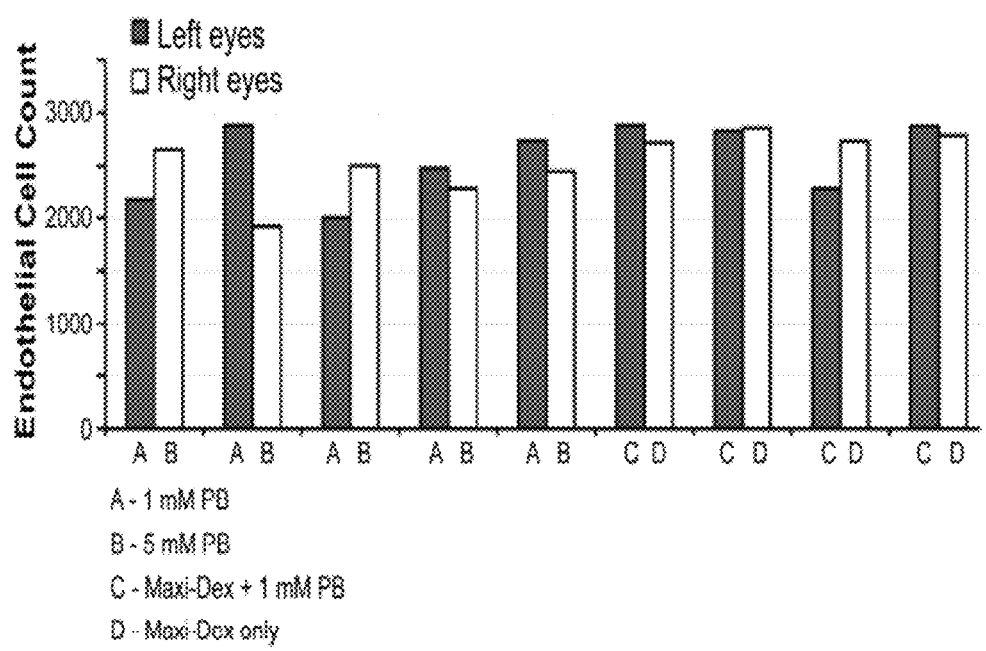
FIG. 8 is a chart on the showing the effect of topical sodium phenylbutyrate on the corneal endothelial cell count of the rabbits.

No adverse ocular or systemic effects were found with regard to the application of sodium phenylbutyrate to the rabbit eye. Specifically, there was no evidence of conjunctival hyperemia, corneal epithelial erosion and/or endothelial cell loss after topical application of sodium phenylbutyrate. Adult male rabbits (n=13) received topical sodium phenylbutyrate (1 and 5 mM) 4 times a day in both eyes. They were examined 3 times a day and none of them exhibited diarrhea, paralysis, convulsions/seizures, bleeding and/or death during the 7-day post-treatment study period. The rabbit eyes were examined by an ophthalmologist on days 7 and 14 in which the rabbits were anesthetized with intramuscular injection of ketamine (75 mg/kg) and xylazine (7.5 mg/kg). No ocular surface (conjunctiva and cornea) diseases such as hyperemia, swelling, inflammation, ulcers and/or bleeding were identified after treatment with PB. Slit lamp biomicroscopy with fluorescein staining did not reveal any defects in the conjunctiva or the cornea. The diagram shows that PB did not cause any significant change in corneal endothelial cell density, as measured by specular microscopy (FIG. 8).

Figure 9:
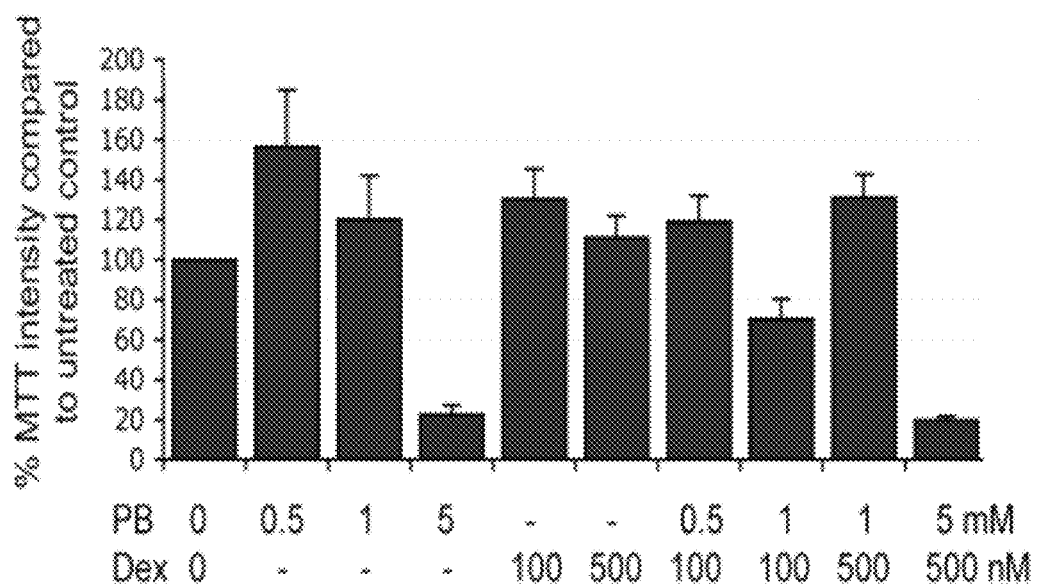
FIG. 9 is a bar-chart showing the effect of sodium phenylbutyrate on cultured human trabecular meshwork cells.

No cytotoxic effect of sodium phenylbutyrate (0.5 and 1 mM) to the cultured human trabecular meshwork (TM) cells was identified (FIG. 9). In these tests, cultured human TM cells (7000 cells/ml) were plated in each well in Dulbecco's Modified Eagle medium (DMEM) supplemented with 1000 mg/L glucose, 2% charcoal-stripped fetal bovine serum and antibiotics. They were treated with sodium phenylbutyrate (PB) (0.5, 1 and 5 mM), dexamethasone (Dex) (100 and 500 nM) and a combination of both for 5 days. Using the 3-(4,5-Dimethylthiazol-2-yl)-2,5-diphenyltetrazolium bromide dye (MTT) cell viability/proliferation assay (Invitrogen), the formazan intensity was measured with a multiplate reader at an excitation wavelength of 595 nm and an emission wavelength 610 nm. The mean signal intensity was expressed as a percentage and was compared to the untreated control among treatments. It was found that PB in the concentrations of 0.5 mM and 1 mM was not cytotoxic to the trabecular meshwork cells. Similar results were found for Dex in concentrations of 100 nM and 500 nM.

Figures 10A, 10B, 10C, 10D:
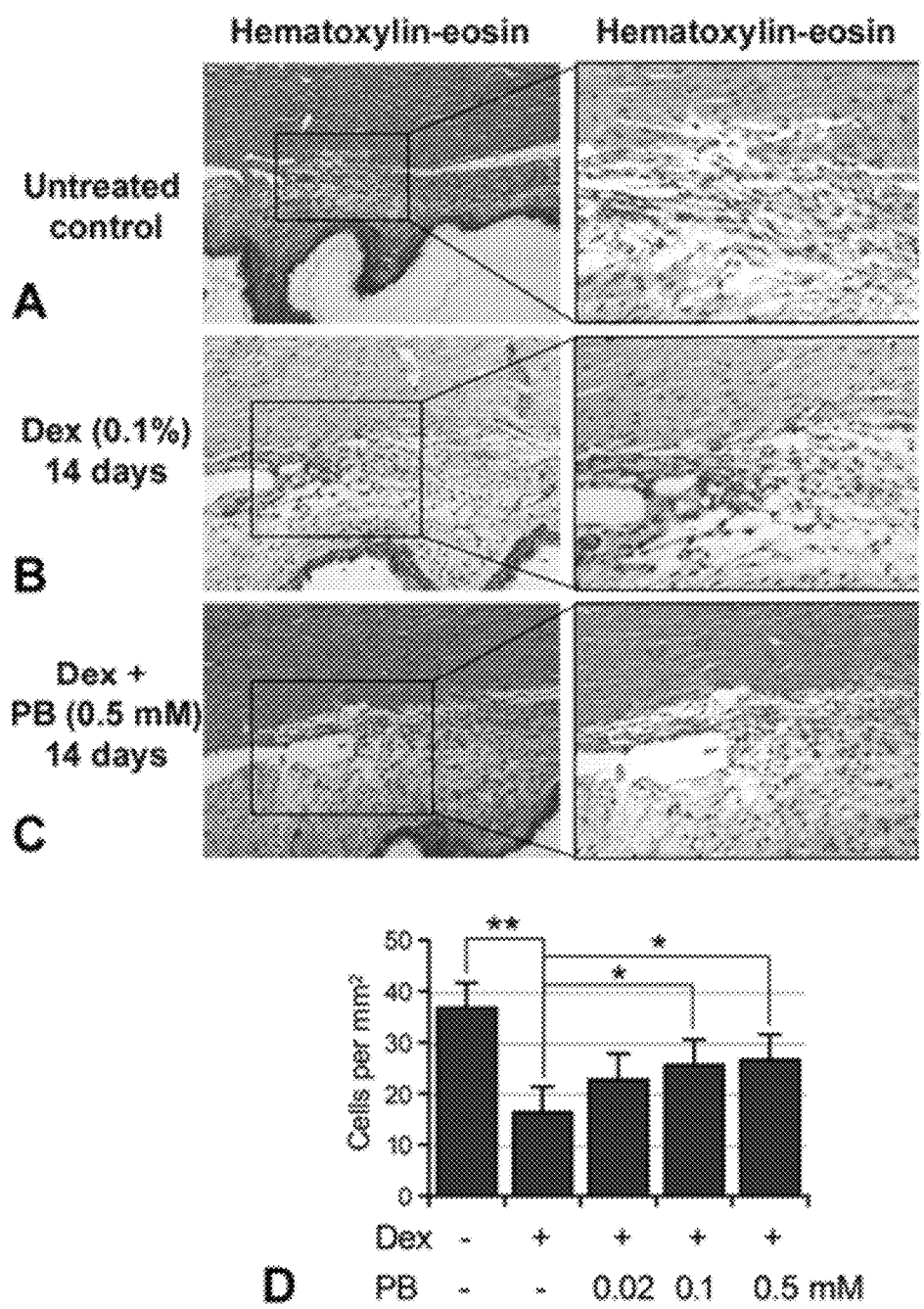
FIGS. 10A-10D are a set of histological images and a bar chart illustrating that sodium phenylbutyrate reduced steroid-induced trabecular meshwork cell loss.
Figures 11A, 11B, 11C:
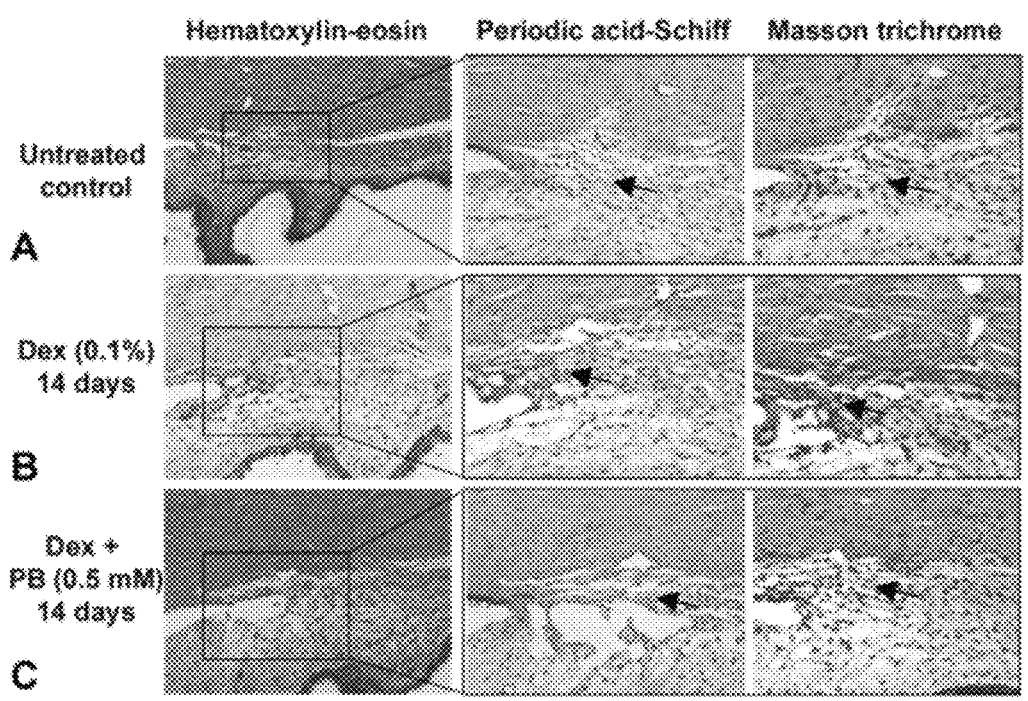
FIGS. 11A-11C are a set of histological images showing that sodium phenylbutyrate reduced extracellular matrix deposition caused by steroid in the trabecular meshwork.

FIGS. 10 and 11 illustrate the structural and anatomical changes in the trabecular meshwork (TM) that provide possible explanation for why sodium phenylbutyrate is able to treat and prevent IOP rise. High IOP is a key feature in glaucoma and partial blockage of the aqueous outflow in the TM is a key reason. When the aqueous outflow passes the drainage openings, the TM cells in the region act as scavengers to clear the debris/deposition which will otherwise block the pathway and hence, resulting in a rise in IOP. While steroid has been shown to damage the TM cells (FIG. 10D) and thus, increase deposition (FIG. 11B) in the aqueous drainage pathway in the TM that will lead to an increase in IOP, PB has been shown in our experiment to reduce the loss of TM cell (FIG. 10D) and maintain a more patent pathway (FIG. 11C) for aqueous drainage.

In relationship to FIG. 10, sodium phenylbutyrate was shown to be able to reduce dexamethasone-induced TM cell loss. The cell density in the TM aqueous outflow region was examined using the Dex and Dex+PB treated rabbit eyes. After topical application of sodium phenylbutyrate (PB) for 14 days, the rabbits were sacrificed. The specimens were paraffin-processed and serially sectioned at a thickness of 5 µm for hematoxylin-eosin histochemistry. Sections of (A) untreated control; (B) treated with Dex, 0.1% for 14 days; and (C) treated with Dex+PB in a concentration of 0.5 mM for 14 days are shown. The number of cells in TM region was quantified and area was measured by Image J software (NIH, US). (D) The cell densities (mean±standard deviation) were compared among the control and treatment groups and P values were calculated by unpaired Student's t-test. In TM region beneath the scleral plexus of veins, a reduction of cell density by 53% was found after treatment with Dex. Such cell loss was reduced by the addition of topical PB in the treatment process. A dose-related correction was found with concentrations varying from 0.02 to 0.5 mM. The percentages of cell loss were 39% for PB in the concentration of 0.02 mM, 31% for PB in the concentration of 0.1 mM and 26% for PB in the concentration of 0.5 mM. These results indicate that PB could reduce the TM cell density reduction induced by steroid (0.1% Dex in this study). With a lesser degree of TM cell loss, the TM aqueous outflow region could be maintained more patent and hence prevent or lessen the steroid-induced intraocular pressure rise.

FIG. 11A-11C illustrates that sodium phenylbutyrate can reduce the extracellular matrix deposition in the aqueous outflow channels in the trabecular meshwork. The steroid-induced intraocular pressure (IOP) rise is secondary to an increased resistance of aqueous outflow, which arises from accumulation and/or deposition of substances such as glycogen and collagen in the extracellular matrix of the trabecular meshwork. An experiment was conducted to determine whether sodium phenylbutyrate (PB) could reduce the amount of glycogen and collagen accumulated in the extracellular matrix of the trabecular meshwork. The extracellular protein and collagen substrate deposited on paraffin sections of TM aqueous outflow region were examined in Dex treated and Dex +PB treated rabbit eyes by special periodic acid-Schiff and Masson trichrome histochemical staining The rabbit eyes were paraffin-processed and serially sectioned at a thickness of 5 µm for histochemistry. Sections of (A) untreated control; (B) treated with Dex (0.1%) for 14 days and (C) treated with Dex (0.1%) +PB (0.5mM) for 14 days are shown. On the paraffin sections of the rabbit eyes with topical dexamethasone with or without sodium phenylbutyrate (1mM) for 14 days, periodic acid-Schiff histochemical staining (FIG. 11, middle column) demonstrated greater deposition of glycogen was found in the intercellular space of the dexamethasone-treated trabecular meshwork region (the arrow in FIG. 11B middle) while the glycogen deposition was greatly reduced in the eyes treated with dexamethasone and sodium phenylbutyrate (1mM, 14 days) (the arrow in FIG. 11C middle). This reduced level resembled that found in the untreated control eyes (the arrow in FIG. 11A middle). For sections with Masson trichrome histochemical staining (FIG. 11, right column), collagen deposit was substantially increased in the dexamethasone-treated trabecular meshwork region (the arrow in FIG. 11 B right) when compared with the untreated control (the arrow in FIG. 11A right). This indicates a possible blockage of aqueous outflow which might lead to a steroid-induced intraocular pressure rise. Reduced collagen stain was noted in the dexamethasone and sodium phenylbutyrate-treated trabecular meshwork region (the arrow in FIG. 11C right). With lesser amount of extracellular matrix deposition in eyes treated with PB, there will be better aqueous drainage and hence, resulting in a lower IOP.

Figures 12A, 12B, 12C, 12D, 12E, 12F:
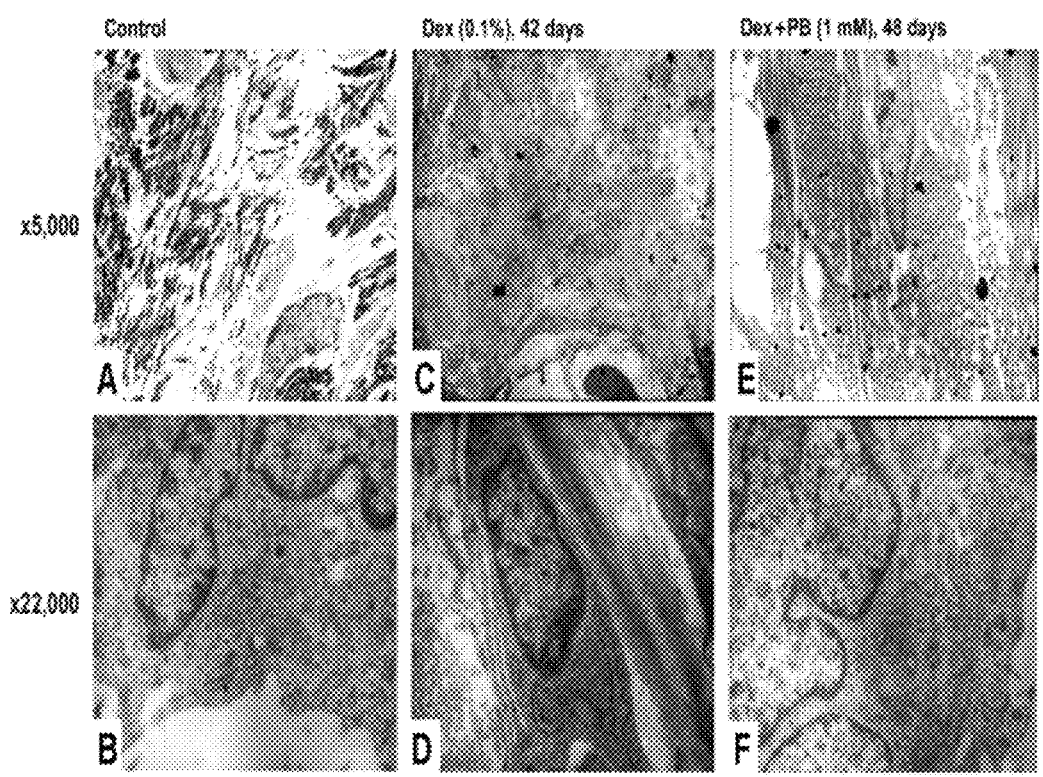
FIG. 12 is a set of electron microscopy images illustrating the effect of sodium phenylbutyrate in the trabecular meshwork.

FIGS. 12A-12F show electron microscopy of the trabecular meshwork (TM) of rabbit eyes. The ultrastructural morphology of rabbit trabecular meshwork (TM) tissues was examined in untreated control eyes, dexamethasone (Dex) (0.1%) treated eyes and Dex+PB (1 mM) treated eyes by transmission electron microscopy. In the control TM region, clear extracellular matrix region was observed in the open aqueous outflow channels. The normal rabbit trabecular meshwork is shown in FIGS. 12A and B. It consists of bundles of fine fibers (elastic and collagen fibers) of the trabecular cells (FIG. 12A). Very rarely, extracellular matrix plaques were observed in this region. At higher magnification, various subcellular organelles, including the nucleus, rough endoplasmic reticulum and mitochondria, appeared normal and without morphological defects (FIG. 12B). In the trabecular meshwork of rabbit eyes treated with topical 0.1% dexamethasone for 42 days, there was deposition of electron dense materials (FIG. 12C). At higher magnification, the cells contained enlarged cisternae of rough endoplasmic reticulum and there were sheaths of basement membrane-like material located in the intercellular space (FIG. 12D). Some nuclei appeared to have more heterochromatin, indicating low cell activity. The deposition was not apparent when there was concurrent topical application of 1 mM sodium phenylbutyrate for 48 days (FIG. 12E). A reduction in extracellular matrix plaques among the trabecular fiber bundles was observed. The outflow channel was clear and was similar to that in the control eyes. At higher magnification, the rough endoplasmic reticulum appeared to be normal and without dilatation (FIG. 12F). Other organelles, such as mitochondria and nucleus, appeared normal as well.

The invention may be characterized as a method for prevention and treatment of conditions of the eye, namely ocular hypertension and primary glaucoma, with a pharmaceutically acceptable compound containing 4-phenylbutyrate sufficient to impede intraocular pressure elevation and/or treat glaucoma. More specifically it may be used for reducing intraocular pressure in patients with ocular hypertension and secondary glaucoma, also for the condition of steroid-induced elevation of intraocular pressure and secondary glaucoma.

The method includes administering the compound through topical application to the eye through one of eye drops, eye lotion, and eye cream, and alternatively, the compound is administrated through one of subconjunctival, subtenon, anterior chamber and intravitreal injection, or wherein the compound is administered one of orally, through skin patches and systemically through injections.

The concentration of sodium phenylbutyrate to be used topically in the compound ranges from 0.01 mM to 15 mM its topical application frequency ranges from one to five times a day.

The compound may be a metabolite of sodium phenylbutyrate, including but not limited to phenylacetate and acetylglutamine or a prodrug of sodium phenylbutyrate or the like salt of phenylbutyrate. The concentration of any of the metabolites of the salt of phenylbutyrate to be used in the compound is the equivalent of the concentration of the salt of phenylbutyrate.

Salts of phenylbutyrate can be formulated for controlled or sustained release with a more convenient dosing.

The phenylbutyrate salt, particularly sodium phenylbutyrate, exerts its biological activity in reducing intraocular pressure rise in conjunction with sympathetic nerve stimulants (nonselective stimulants such as epinephrine and alpha2 stimulants such as apraclonidine), sympathetic nerve blockers (beta blockers including timolol, befunolol, carteolol, nipradilol, betaxolol, levobunolol, and metipranolol and alpha1 blockers such as bunazosin hydrochloride), parasympathetic nerve agonists (pilocarpine), carbonic anhydrase inhibitors (acetazolamide and dorzolamide), prostaglandin analogue (isopropyl unoprostone, latanoprost, travoprost, bimatoprost), and cortisol-derived compounds, and the like.

The phenylbutyrate salt, its metabolites, or prodrugs can be formulated with anti-inflammatory steroid in eye-drops, injection, controlled or sustained release methods such as in slow-release drug implant, or impregnated in degradable material formats (subconjunctival, subtenon, intracameral (injecting into the anterior chamber of the eye), or intravitreal) to prevent and treat the steroid-induced increase in intraocular pressure.

The invention has been explained with reference to specific embodiments. Other embodiments will be evident to those of skill in the art. It is therefore not intended that the invention be limited, except as indicated by the appended claims.

What is claimed is:

1. A medication comprising (i) a carrier; and (ii) a pharmaceutically acceptable salt of 4-phenylbutyrate in a concentration range from 0.02 mM to 0.5 mM, wherein the medication is in a form suitable for topical application to eyes and is formulated into an eye drop, eye lotion, or eye cream.

2. The medication according to claim 1, wherein the medication further comprises an anti-inflammatory steroid.

3. The medication according to claim 1, wherein the pharmaceutically acceptable salt of 4-phenylbutyrate is sodium 4-phenylbutyrate.

4. The medication according to claim 3, wherein the concentration of sodium 4-phenylbutyrate is 0.02 mM, 0.1 mM, or 0.5 mM.

5. A method for treatment of intraocular pressure elevation in a patient, comprising administering the medication of claim 1 to the patient.

6. The method of claim 5, wherein the medication is administered one to five times a day.

7. The method of claim 5, wherein the pharmaceutically acceptable salt of 4-phenylbutyrate is sodium 4-phenylbutyrate.

8. The method of claim 5, further comprising administering to the patient a sympathetic nerve stimulant, sympathetic nerve blocker, parasympathetic nerve agonist, carbonic anhydrase inhibitor, prostaglandin analogue, or cortisol-derived compound.

9. The method of claim 5, further comprising administering to the patient an anti-inflammatory steroid.

10. The method of claim 5, wherein the medication is formulated for controlled or sustained release of the pharmaceutically acceptable salt of 4-phenylbutyrate.

* * * * *